US006479050B1

(12) United States Patent
van den Berghe

(10) Patent No.: US 6,479,050 B1
(45) Date of Patent: Nov. 12, 2002

(54) TRACE ELEMENT-RICH ADDITIVE, METHOD FOR PREPARING SAME, PREPARATION IN WHICH THE ADDITIVE IS INCLUDED AND USE THEREOF

(75) Inventor: Dirk A. van den Berghe, Laarne (BE)

(73) Assignee: Innovi N.V., Zaventem (BE)

( * ) Notice: Subject to any disclaimer, the term of this patent is extended or adjusted under 35 U.S.C. 154(b) by 0 days.

(21) Appl. No.: 08/157,037

(22) PCT Filed: Jun. 3, 1992

(86) PCT No.: PCT/EP92/01328
§ 371 (c)(1),
(2), (4) Date: Mar. 22, 1994

(87) PCT Pub. No.: WO92/21749
PCT Pub. Date: Dec. 10, 1992

(30) Foreign Application Priority Data

Jun. 3, 1991 (EP) ............................................ 91201350

(51) Int. Cl.[7] ................................................ A01N 63/00
(52) U.S. Cl. ................ 424/93.45; 424/93.4; 435/252.1; 435/168; 426/74; 426/61
(58) Field of Search .............................. 424/93 J, 93 D, 424/93 R, 93 Q, 93.44, 93.45, 93.4; 426/60, 61; 435/252.1, 804, 254.1, 168

(56) References Cited

U.S. PATENT DOCUMENTS 5,185,165 A * 2/1993 Lynn ........................... 426/61

FOREIGN PATENT DOCUMENTS

| EP | 0181170 | 11/1985 | .......... A61K/35/74 |
| GB | 2233666 | 5/1990 | ............ C21N/1/20 |
| WO | 8102242 | 8/1981 | ............ C05D/9/02 |

OTHER PUBLICATIONS

Friend et al., J. Applied Nutrition, 36:2, pp. 125–153 (1984).*
Fritz et al., J Environ Qual 17 (3). 1988. 480–484.*
Shahani et l., 1980, Am. J. Clin. Nutr., 33:2448–2457.*
Webster's Dictionary, 1986, Merriam Webster, 9th Ed, p. 157.*
Wadge, A, *Plant and Soil*, vol. 96, p. 407–412, 1986.*
Gunner et al. J. of Bacteriol., vol. 87, 1964 p. 1309–1316.*
ATCC Catalogue of Bacteria, 1992, p. 172.*
Lindblow–Kull et al., Biochem, Biophys. Res. Comm., vol. 93, 1980 p. 572–576.*
WPIL / Derwent Abstract J62134083.
Patent Abstracts of Japan, vol. 9, No. 205 dated August 22, 1985.
Patent Abstract of Japan, vol. 11, No. 300 dated Sep. 29, 1987.

* cited by examiner

*Primary Examiner*—Irene Marx
(74) *Attorney, Agent, or Firm*—Webb Ziesenheim Logsdon Orkin & Hanson, P.C.

(57) ABSTRACT

The invention provides a method for preparing an additive that is rich in trace-elements, which method comprises the steps of: a) providing a culture medium to which the trace element or compound thereof is additionally added: b) culturing the micro-organism in the culture medium such that the micro-organism accumulates the trace-element: c) separating the trace-element from the culture. The method is particularly useful with Lactobacillus-species for the accumulation of selenium. The invention further provides an additive prepared according to the method of the invention, a food preparation and a therapeutic preparation containing the additive, and the use of the additive for treating trace element deficiencies.

13 Claims, No Drawings

TRACE ELEMENT-RICH ADDITIVE, METHOD FOR PREPARING SAME, PREPARATION IN WHICH THE ADDITIVE IS INCLUDED AND USE THEREOF

The invention relates to a method for preparing an additive that is rich in trace elements. The invention further relates to an additive obtained in this manner, a food preparation and a therapeutic preparation in which the additive is included, and use of the additive.

The human and animal body can begin to exhibit diverse disorders in the case of a chronic deficiency of trace elements, such as seleneium, manganese, copper, zinc, cobalt, iron, nickel, chromium and the like. It is known that the diets of for example infants, children, hospitalitized patients with artificial feeding, geriatric patients and the like are often deficient in selenium. Food is the main source of selenium (Se) for humans. Low Se content in food will therefore unavoidably lead to a decreased Se concentration in the body.

In individuals who are fed totally parenterally (with purified preparations) and who take no oral nutrition for a long period, it is observed for example that they develop a Se deficiency, since total parenteral nutrition (TPN) contains practically no Se. Reduced Se levels and glutathione-peroxidase activities in the blood are therefore found in patients who receive protracted TPN. The attendant clinical symptoms are muscle weakness, heart rhythm disorders, arthritis, change of hair colour, whitening of the nails and increase of the creatine phospokinase activity in plasma. Addition of Se to the food results in an increase of the Se concentration and the GSH-Px activity as well as the removal of the clinical symptoms.

Deficiency likewise occurs in patients who receive synthetic elementary nutrition. These include among others patients with hereditary metabolic disorders. The treatment of patients with metabolic disorders consists of following determined diets which are mostly limited in proteins and to which essential amino-acids are added. In Germany it has been found that such diets contain very low Se contents.

Keshan disease—a juvenile cardiomyopathy, which occurs in young women and children living in Se deficient areas in China—is likewise the result of a reduced intake of Se. Although Se deficiency is probably not the only cause of this illness, all these patients exhibit low Se concentrations in hair and plasma, and the illness is cured by adequate supplementation with selenite.

A number of possibilities exist to counteract Se deficiency in patients sensitive thereto.

Firstly, inorganic selenium in the form of selenite or selenate can be administered to patients. The results which have been obtained for example in China with Keshan disease are very positive. An important drawback however is that the inorganic selenite can cause toxic symptoms in certain cases of weakened condition, such as deficiency of trace elements other than selenium or protein deficiency. Another possibility is the administering of seleno-methionine preparations. This product is absorbed in the body in the same manner as methionine. A great drawback of seleno-methionine is that it is quite rapidly absorbed into various proteins, also into those proteins which normally speaking are not selenated. This can be dangerous, particularly for infants who still have to build up most of the cells. Furthermore, seleno-methionine preparations are expensive.

A third known form of administering selenium is yeast with a high selenium content. However, a number of drawbacks are likewise found to be linked hereto. On the one hand this is the occurrence of urticaria as an allergic reaction to the yeast cells and the presence in the yeast cells of mitogenic polysaccharides which can be dangerous for weakened patients. On the other hand selenium in yeast is mostly found to have the form of seleno-methionine. The drawbacks thereof have already been described for seleno-methionine preparations. An excessive supply of seleno-methionine could in the long term also be harmful for the quality of non-reproducing proteins and cells such as brain cells.

It is therefore the object of the present invention to provide a method for preparing an additive that is rich in at least one trace element such as selenium, with which method an additive is obtained which does not have the above stated drawbacks.

The invention achieves this through a method which comprises the steps of:
a) providing a culture medium to which the trace element or a compound thereof is additionally added;
b) culturing a micro-organism in the culture medium such that the micro-organism accumulates the trace element; and
c) separating the micro-organism from the culture medium.

With the method according to the present invention an additive is abtained which consists of purified micro-organisms which contain an increased content of at least one trace element. The micro-organism will have been accumulated every trace element offered in the culture medium in the form of various organic and anorganic compounds. Naturally occurring food fermentation bacteria are preferably used which will not colonize the intestine, such as for example bacteria of the genus Lactobacillus. In addition to L. casei and L. plantarum, L. delbrueckii sbsp. bulgaricus can be used. It is however also possible to use micro-organisms that occur in food products like milk and which do colonize the intestine.

Experiments have shown that particularly Lactobacillus delbrueckii sbsp. bulgaricus (deposit available from American Type Culture Collection No. ATCC 11842, American Type Culture Collection, 12301 Parklawn Drive, Rockville, Md. 20852, USA) in its log phase in a medium to which selenium is added as the trace element incorporates a constant quantity of selenium, this in the form of both organic and inorganic compounds. Selenium is substantially accumulated in the form of seleno-cystein. Seleno-cystein is the $23^{rd}$ amino acid having its own tRNA and its own codon encoded on the DNA. It has been found that bacteria of the genus Lactobacillus are seleno-bacteria capable of producing seleno-cystein out of anorganic selenium compounds. Seleno-cystein is incorporated in selenated proteins. The natural selenium compounds produced by the bacteria, such as selenated proteins are offered to the intestinal cells which can make a choice for themselves. Due to a varied supply of selenium compounds the above stated problems, such as toxicity, can be avoided. The bacteria themselves will never accumulate an excess of seleno-proteins. In contrast to seleno-methionine, particular accents are placed in the selenating of proteins during use of the micro-organisms according to the invention. Through an as yet unspecified mechanism the selenite is incorporated into well-specified seleno-proteins. Just as the other seleno-compounds from the bacteria, these proteins are found to be well metabolized by humans and animals.

In addition the bacteria contain vitamins, trace elements and proteins. These substances not only have a positive effect on the individual taking in the bacteria but also make it possible that selenium can follow its own specific path and antagonism is possible.

The Lactobacillus bacteria are not toxic. *Lactobacillus delbrueckii sbsp. bulgaricus* is moreover known to exhibit anti-tumour action, to balance the intestinal bacteria and to detoxify a number of heavy metals such as mercury, lead and cadmium. *L. delbrueckii sbsp. bulgaricus* does not colonize the intestine. Furthermore the culture of *L. delbrueckii sbsp. Bulgaricus* at 45° C. in an acidic environment counteracts the growth of pathogens.

The additive obtained with the method according to the present invention can for example be prepared by culturing *L. delbrueckii sbsp. bulgaricus* in a culture medium to which a determined amount of a selenium compound is added. A maximum of 3 µg/ml selenite is preferably added. A very suitable culture medium for *L. delbrueckii sbsp. bulgaricus* is whey, a by-product of cheese manufacture. The whey is preferably first rid of proteins because they have the tendency to precipitate. An additional advantage of removing the proteins is that the final additive will contain virtually no free proteins, whereby it becomes suitable for administering to patients with a protein restricted diet.

The micro-organisms are preferably separated from the culture medium such that they remain intact. This separation can take place by means of centrifuging or filtration.

The selenium status of a cell regulates the glutathione-peroxidase activity, a seleno-enzyme that protects against oxidative stress and ageing. An increase of selenium causes an increased glutathione-peroxidase activity and an excess of glutathione-peroxidase mRNA. It is generally assumed that it is important to bring the glutathione-peroxidase activity to a constant level. Particularly in the case of infants this plateau must be reached rapidly in order to ensure an optimal protection against oxidative stress. Experiments have shown that the additive according to the present inventions allows the glutathione-peroxidase activity to rise very rapidly at a low concentration of the additive.

The additive according to the invention is found to be tolerated well by children with a protein restricted diet. The absorption of the selenium compounds into the blood is found to proceed as well as the absorption of selenite, selenate, seleno-methionine and seleno-yeast, without the drawbacks related to these selenium compounds occurring.

It has likewise been found that selenium in the additive according to the invention occurs particularly in the form of seleno-cysteine or a derivative thereof instead of seleno-methionine. In view of the drawbacks linked to seleno-methionine, namely a non-specific selenating of proteins, this is an important property. In addition it is assumed that seleno-cysteine, like selenite, exhibits a direct or indirect anti-tumor activity. This is in contrast to seleno-methionine.

Finally, the additive according to the invention also has the advantages of the use of *L. delbrueckii sbsp. bulgaricus*, namely anti-tumour activity and adhering of heavy metals to the cell wall of the bacteria. A portion of the selenite to which the bacteria have been exposed during culture is situated on the cell wall in the form of elementary selenium and in this manner detoxified mercury.

The additive according to the present invention can be administered in different forms. One possibility is adding the additive to a foodstuff. Very suitable are those foodstuffs which naturally already contain Lactobacillus species, such as dairy products. An example of this is margarine.

It is further possible to administer the additive in the form of a therapeutic preparation. Such a preparation will contain an active quantity of the additive and, if desired, suitable dilution and carrier materials. Such a therapeutic preparation can be used for eliminating a trace element deficiency or even in the case of illnesses, such as immunological deficiency, immunological stress, cardiovascular disorders, thyroid gland disorders, asthma, intoxication, muscle disorders, blood disorders, neurological degenerative disorders and for the prevention of cancer and symptoms of ageing. The preparation will have a suitable form for administering.

The action of the additive obtained by means of the method according to the present invention is illustrated in the examples below.

EXAMPLE 1

Weight increase of mice with an Se deficient diet.

Administered to a number of groups of mice with an Se deficient diet were different concentrations of seleno-methionine ($10^{-4}$, $10^{-5}$, $10^{-6}$ and $10^{-7}$ M), seleno-cystine ($10^{-4}$, $10^{-5}$, $10^{-6}$ and $10^{-7}$ M) and the additive according to the present invention ($10^{-5}$, and $10^{-7}$ M). The mice to which the additive according to the invention was administered were found to display a greated weight increase (see figure).

EXAMPLE 2

In vivo effect to the additive according to the invention on the glutathione-peroxidase activity in plasma.

For three weeks a quantity of 3 microgrammes of Se in the form of the additive according to the invention was administered daily to a three-year-old girl suffering from Protein Lysine Intolerance (PLI). During this supplementation an increase in the Se content and glutathione peroxidase activity in the plasma was recorde (see table). With a second supplementation with selenite after 13 months no increase of the Se content and glutathione activity was observed (see table).

TABLE

| supplement | glutathione-peroxidase activity (U/ml) | Se-content (ng/ml) |
| --- | --- | --- |
| none | 0.11 | 20 |
| none | 0.12 | 10 |
| *L. delbrueckii* sbsp. *bulgaricus*-Se | 0.19 | 16 |
| *L. delbrueckii* sbsp. *bulgaricus*-Se | 0.34 | 27 |
| *L. delbrueckii* sbsp. *bulgaricus*-Se | 0.19 | 35 |
| *L. delbrueckii* sbsp. *bulgaricus*-Se | 0.28 | 32 |
| none | 0.13 | 21 |
| none | 0.17 | 22 |
| none | 0.14 | 22 |
| selenite | 0.13 | 20 |
| selenite | 0.12 | 22 |
| selenite | 0.13 | 24 |
| selenite | 0.13 | 23 |

What is claimed is:

1. A method of preparing a food additive, containing bacteria having incorporated the trace element selenium, comprising the steps of:
   a) providing a culture medium to which the trace element selenium is added in the form of selenite in a concentration ranging from >0 µg/ml to 3 µg/ml;
   b) culturing *Lactobacillus delbrueckii* bacteria in the culture medium such that the bacteria incorporate selenium as seleno-cysteine; and
   c) separating the bacteria from the culture medium.

2. The method as claimed in claim 1, wherein the *Lactobacillus delbrueckii* bacteria is *Lactobacillus delbrueckii sbsp. bulgaricus.*

3. The method as claimed in claim 1, wherein at least one additional trace element is added to the culture medium.

4. The method as claimed in 3, wherein the additional trace element is selected from the group consisting of manganese, zinc, copper, cobalt, iron, nickel, chromium, or combinations thereof.

5. The method as claimed in claim 1, wherein the food additive has a selenium content of 100 to 1000 µg Se/gram dry weight.

6. The method as claimed in claim 1, wherein the culture medium is whey.

7. The method as claimed in claim 1, wherein the bacteria are separated from the culture medium such that they remain intact during separation.

8. The method as claimed in claim 7, wherein the bacteria are separated from the culture medium by means of filtration or centrifuging.

9. A food additive containing bacteria having incorporated the trace element selenium wherein the bacteria are prepared by a method comprising the steps of:

a) providing a culture medium to which the trace element selenium is added in the form of selenite in a concentration ranging from >0 µg/ml to 3 µg/ml;

culturing *Lactobacillus delbrueckii* bacteria in the culture medium such that the bacteria incorporate selenium as seleno-cysteine; and separating the bacteria from the culture medium.

10. The food additive as claimed in claim 9, wherein the bacteria belong to the species *Lactobacillus delbrueckii sbsp. bulgaricus*.

11. A food item comprising a foodstuff and the food additive as claimed in claim 9.

12. A food item as claimed in claim 11, wherein the foodstuff is a dairy product.

13. A food item as claimed in claim 12, wherein the dairy product is margarine.

* * * * *

UNITED STATES PATENT AND TRADEMARK OFFICE
CERTIFICATE OF CORRECTION

PATENT NO.   : 6,479,050 B1
DATED        : November 12, 2002
INVENTOR(S)  : Dirk A. van den Berghe It is certified that error appears in the above-identified patent and that said Letters Patent is hereby corrected as shown below:

<u>Title page,</u>
Item [56], References Cited, OTHER PUBLICATIONS, "Shahani et l." should read
-- Shahani et al. --.

<u>Column 6,</u>
Line 4, before "culturing" insert -- b) --.
Line 7, before "separating" insert -- c) --.

Signed and Sealed this

Seventeenth Day of June, 2003

JAMES E. ROGAN
*Director of the United States Patent and Trademark Office*